US010231990B2

(12) United States Patent
Claret et al.

(10) Patent No.: US 10,231,990 B2
(45) Date of Patent: Mar. 19, 2019

(54) PRESERVATIVE-FREE COMPOSITION FOR TOPICAL USE INCLUDING HYALURONIC ACID

(75) Inventors: Claude Claret, Nice (FR); Martine Claret, Nice (FR); Carole Gard, Le Cannet (FR)

(73) Assignee: Horus Pharma, Saint-Laurent-du-Var (FR)

(*) Notice: Subject to any disclaimer, the term of this patent is extended or adjusted under 35 U.S.C. 154(b) by 0 days.

(21) Appl. No.: 13/812,671

(22) PCT Filed: Jul. 28, 2011

(86) PCT No.: PCT/EP2011/062971
§ 371 (c)(1),
(2), (4) Date: Jan. 28, 2013

(87) PCT Pub. No.: WO2012/013736
PCT Pub. Date: Feb. 2, 2012

(65) Prior Publication Data
US 2013/0129844 A1 May 23, 2013

(30) Foreign Application Priority Data
Jul. 28, 2010 (FR) ...................................... 10 56221

(51) Int. Cl.
A61K 31/728 (2006.01)
A61K 8/73 (2006.01)
A61K 8/97 (2017.01)
A61K 31/07 (2006.01)
A61K 31/4164 (2006.01)
A61K 31/70 (2006.01)
A61K 31/7016 (2006.01)
A61K 36/00 (2006.01)
A61K 45/06 (2006.01)
A61Q 19/00 (2006.01)

(52) U.S. Cl.
CPC ............ A61K 31/728 (2013.01); A61K 8/735 (2013.01); A61K 8/97 (2013.01); A61K 31/07 (2013.01); A61K 31/4164 (2013.01); A61K 31/70 (2013.01); A61K 31/7016 (2013.01); A61K 36/00 (2013.01); A61K 45/06 (2013.01); A61Q 19/005 (2013.01); A61Q 19/007 (2013.01); A61K 2800/75 (2013.01)

(58) Field of Classification Search
None
See application file for complete search history.

(56) References Cited

U.S. PATENT DOCUMENTS

| 4,141,973 | A | * | 2/1979 | Balazs | ................ C08B 37/0072 514/54 |
| 4,780,414 | A | * | 10/1988 | Nimrod | .................. A61K 8/735 435/101 |
| 4,900,550 | A | * | 2/1990 | Lowry | ......................... 424/744 |
| 5,011,695 | A | * | 4/1991 | Dichtelmuller | ........ A61K 31/07 422/28 |
| 5,232,687 | A | | 8/1993 | Geimer | |
| 5,409,904 | A | * | 4/1995 | Hecht | .................. A61K 9/0048 514/23 |
| 2007/0210121 | A1 | | 9/2007 | Stadelhofer et al. | |
| 2009/0294347 | A1 | | 12/2009 | Wochele et al. | |

FOREIGN PATENT DOCUMENTS

| CN | 1628695 A | * | 6/2005 |
| DE | 3419255 | | 2/1985 |
| EP | 1270013 A1 | | 1/2003 |
| EP | 2085068 | | 8/2009 |
| FR | 2816600 | | 11/2000 |
| FR | 2873358 | | 7/2004 |
| WO | 2008/015505 | | 2/2008 |

OTHER PUBLICATIONS

Office Action issued for corresponding Russian Patent Application No. 2013158701, dated May 23, 2016.
English Translation of Office Action issued for corresponding Russian Patent Application No. 2013158701, dated May 23, 2016.

* cited by examiner

Primary Examiner — Terry A McKelvey
Assistant Examiner — Catheryne Chen
(74) Attorney, Agent, or Firm — Banner & Witcoff, Ltd.

(57) ABSTRACT

The present invention relates to a sterile and/or decontaminated composition for topical use, including hyaluronic acid at a concentration of greater than or equal to 0.1 wt % relative to the total weight of the composition, at least one skin wound healing agent, optionally at least one plant extract, and at least one solvent. The invention also relates to a unit including such a composition, to a method for preparing such a composition, and to the uses thereof.

5 Claims, No Drawings

PRESERVATIVE-FREE COMPOSITION FOR TOPICAL USE INCLUDING HYALURONIC ACID

RELATED APPLICATION DATA

This application is a National Stage Application under 35 U.S.C. 371 of co-pending PCT application PCT/EP2011/062971 designating the United States and filed Jul. 28, 2011; which claims the benefit of FR patent application number 1056221 and filed Jul. 28, 2010 each of which are hereby incorporated by reference in their entireties.

The present invention relates to compositions for topical use comprising hyaluronic acid, in particular free of preservatives, to the uses of same and to a method for obtaining same.

The composition can particularly be intended for topical application, in particular on fragile skin and/or mucous membranes, in particular those protecting the eye.

The eyebrows, lashes and eyelids are essential elements of the eye's protective system. In particular, the eyelids constitute a barrier that protects the eyeball from injury. The skin covering the eyelid is very sensitive, very thin and must be kept relatively well hydrated.

Skin permeability has been widely studied in dermatology and depends on many factors, including thickness and degree of hydration. Thus, any composition applied to tissue near the eyeball will be likely to enter the eye as well.

This is confirmed by the few studies relating to local anesthesia of the eyelids using EMLA (lidocaine/prilocalne) cream, and the ocular toxicity induced, as well as by the consequences to the eye of the use of certain cosmetics such as kohl, mascara, etc.

Furthermore, the conjunctiva of the eyelid, the palpebral conjunctiva, which covers the anterior part of the eye, is sensitive to the adverse effects of preservatives present in compositions, such as BAK or thiomersal. Indeed, these can lead to various adverse effects, such as conjunctival hyperemia and an allergic reaction.

It is thus desirable to have compositions that are free of, or that limit these adverse effects while enabling topical use on fragile and/or injured skin and/or mucous membranes.

Hyaluronic acid is a major compound of the skin. It is notably useful in the repair of injured skin and mucous membranes.

The existing compositions for topical use that include hyaluronic acid have in general a relatively low content of hyaluronic acid, hyaluronic acids of insufficient molecular weight, an unsatisfactory viscosity, many compounds and texturing agents, chemical preservatives and substances with antiseptic or surfactant properties possibly incompatible or likely to cause irritant or adverse effects with the mucous membranes and/or the skin, in particular certain injured skin, ocular tissues and their related structures.

In particular, in the case of topical use of these compositions on fragile skin or mucous membranes, the compositions of the prior art can have the disadvantage of a washing and/or a protection, for example of the eyelids, that is insufficient, of a prevention and/or a treatment, notably of eye dryness, that is unsatisfactory, and/or problems of active sensitization via the introduction of allergens, for example due to the presence of multiple compounds.

The compositions of the prior art may also include a large number of compounds. This large number of compounds can lead to undesirable synergies and to cytotoxicity that is too high, notably related to the presence of preservatives and antiseptic compounds, such as essential oils, that can present risks of adverse effects. These types of adverse effects can be particularly notable on certain areas of cutaneous tissues such as, for example, tissues of the face and the hands, more frequently exposed to injury from the environment, or tissues of the eyelids.

It is thus desirable to obtain a composition with good effectiveness, in particular in the terms set out above, for example of washing, protection, prevention and/or treatment, while having a minimum of adverse effects, notably such as those set out above.

Furthermore, the methods for sterilizing or decontaminating a formula, such as chemical sterilization, via the use of chemical agents and/or preservatives in the formula, ionizing sterilization or sterilization by heating have a certain number of disadvantages notably in the case of the preparation of a composition including hyaluronic acid, in particular when the hyaluronic acid is present at a relatively high concentration and/or has a high molecular weight.

For example, chemical sterilization is relatively or even completely incompatible with use of the composition on injured tissues or mucous membranes.

Ionizing sterilization can cause the partial deterioration, even the total destruction, of certain products within the composition, including hyaluronic acid in particular.

Decontamination or sterilization methods that include sterilization by heating of the product at temperatures greater than or equal to 120° C. can affect the integrity of the packaging and/or the properties of the ingredients.

Lastly, when low decontamination or sterilization temperatures, notably below or equal to 80° C., are used it is generally necessary to then refrigerate the product. Consequently, the product obtained often has a short shelf life.

Thus, the present invention aims at solving the problems described above in whole or in part. In particular, the invention aims to provide a composition with good effectiveness, that is easy to obtain, with few or no adverse effects and with satisfactory preservation conditions and duration, notably at room temperature, and to provide a simple method for obtaining one such composition.

According to a first aspect, the present invention relates to a composition, notably sterile and/or decontaminated, for topical use comprising, or consisting of:
  hyaluronic acid at a concentration greater than or equal to 0.1% by weight in relation to the total weight of the composition, and
  at least one skin cicatrization agent,
  optionally a plant extract, notably having medicinal and/or pharmaceutical properties, and
  at least one solvent.

In the context of the present invention, the term "decontaminated" means that tests of microbiological cleanliness are carried out according to the criteria of the ISO standard 21149, either by enumeration of the aerobic flora (less than 1 CFU/ml), the absence of *Pseudomonas aeruginosa*, the absence of *Staphylococcus aureus* and the absence of *Candida albicans*.

In the context of the present invention, the term "sterile" refers to the absence of bacteria as defined in the European Pharmacopoeia, 6$^{th}$ edition, 2008.

Hyaluronic acid is a disaccharide polymer, formed of D-glucuronic acid and a molecule of N-acetyl-glucosamine.

It is naturally present in many tissues, mainly in the skin, in particular in the epidermis, as well as in the conjunctive tissues, and represents one of the principal components of the extracellular matrix. The length of the molecule varies depending on the tissue, the species and the state of the tissue.

Hyaluronic acid can be obtained by tissue extraction from animal tissues or by bacterial fermentation, notably with *Streptococcus equi* or *Bacillus subtilis*.

The composition comprises hyaluronic acid at a concentration greater than or equal to 0.1% by weight, or a concentration greater than or equal to 0.2% by weight, notably at a concentration greater than or equal to 0.3% by weight, in particular greater than or equal to 0.4% by weight, or greater than or equal to 0.5% by weight in relation to the total weight of the composition.

Particularly, the concentration of hyaluronic acid is from 0.1 to 2% by weight, in particular from 0.2 to 2% by weight, notably from 0.2 to 1% by weight, particularly from 0.2 to 0.5% by weight, in relation to the total weight of the composition.

According to a particular embodiment, the composition has a concentration of hyaluronic acid from 0.1 to 1% by weight, in particular from 0.1 to 0.5% by weight in relation to the total weight of the composition.

The hyaluronic acid can be a mixture of low molecular weight hyaluronic acid and high molecular weight hyaluronic acid.

The high molecular weight hyaluronic acid can have a molecular weight from 10 to 1,200 kDa, notably from 10 to 1,000 kDa, in particular from 10 to 800 kDa.

Particularly, the high molecular weight hyaluronic acid has a molecular weight from 600 to 1,200 kDa, notably from 800 to 1,200 kDa.

The low molecular weight hyaluronic acid can have a molecular weight from 10 to 1,000 kDa, notably from 10 to 600 kDa.

Particularly, the low molecular weight hyaluronic acid has a molecular weight from 400 to 1,000 kDa, notably from 600 to 1,000 kDa.

When the composition includes both high and low molecular weight hyaluronic acids, the high molecular weight hyaluronic acid has a molecular weight greater than the molecular weight of the low molecular weight hyaluronic acid.

When the composition includes both high and low molecular weight hyaluronic acids, the weight ratio of the high molecular weight hyaluronic acid to the low molecular weight hyaluronic acid can range from 1,000 to 1, notably from 500 to 2, in particular from 100 to 5, or from 50 to 10.

According to another embodiment, when the composition includes both high and low molecular weight hyaluronic acids, the weight ratio of the high molecular weight hyaluronic acid to the low molecular weight hyaluronic acid ranges from 10 to 0.1, notably from 5 to 0.2, in particular from 2 to 0.5, or is about 1.

Molecular weight can be measured by the standard HPLC elution/exclusion method.

According to a particular embodiment, the composition includes as hyaluronic acid only high molecular weight hyaluronic acid. This means notably that the weight ratio of the low molecular weight hyaluronic acid to the high molecular weight hyaluronic acid is less than or equal to 0.1%, in particular less than 0.01%, or is 0.

In particular, the composition has a concentration of high molecular weight hyaluronic acid greater than or equal to 0.1% by weight, notably greater than or equal to 0.3% by weight, in particular greater than or equal to 0.4% by weight, or greater than or equal to 0.5% by weight in relation to the total weight of the composition.

In this case, the concentration of high molecular weight hyaluronic acid can range from 0.1 to 2% by weight, in particular from 0.2 to 2% by weight, notably from 0.2 to 1% by weight, particularly from 0.2 to 0.5% by weight, in relation to the total weight of the composition.

According to another variant, the concentration of high molecular weight hyaluronic acid can range from 0.1 to 1% by weight, in particular from 0.1 to 0.5% by weight in relation to the total weight of the composition.

According to one embodiment, the present composition for topical use is free of preservatives, notably chemical preservatives, used alone or in combination. In particular, said composition is free of preservatives selected from the list of the products authorized by regulation, notably selected from:

quaternary ammoniums, notably benzalkonium chloride, alkyldimethylbenzylammonium chloride, cetrimide, cetylpyridinium chloride, benzododecinium bromide, benzethonium chloride, cetalkonium chloride, mercury preservatives, such as phenylmercuric nitrate/acetate/borate, thiomersal, alcohol preservatives, such as chlorobutanol, benzyl alcohol, phenylethanol, phenylethyl alcohol, carboxylic acids, such as sorbic acid, phenols, in particular methyl/propyl paraben, and/or amidines, for example chlorhexidine digluconate.

The composition can indeed be free of EDTA as such or in combination with at least one preservative. EDTA, being a chelating agent potentiating the effectiveness of the preservatives, in combination with at least one preservative.

In the context of the present invention, the expression "free of" refers to a concentration less than or equal to 10 ppm, notably less than or equal to 1 ppm, or equal to 0 ppm.

According to a particular embodiment, the composition includes at least one cicatrization agent, which is a chemical compound that accelerates skin cicatrization and cell regeneration.

The cicatrization agent can be selected from allantoin, vitamin A, sucralfate, which is a polysulfated disaccharide, and/or basic aluminum sucrose sulfate.

The cicatrization agent can be present in a concentration greater than or equal to 0.01% by weight, notably at a concentration greater than or equal to 0.1% by weight, in particular greater than or equal to 0.2% by weight in relation to the total weight of the composition.

Allantoin is a nitrogenized chemical compound of organic or plant origin, produced by the oxidation of uric acid, with healing and regenerative properties. The composition can include a concentration of allantoin greater than or equal to 0.01% by weight, notably a concentration greater than or equal to 0.1% by weight, in particular greater than or equal to 0.2% by weight in relation to the total weight of the composition.

Vitamin A can be present in the form of retinal, retinoic acid or retinal phosphate or palmitate. The composition can include a concentration of vitamin A greater than or equal to 0.01% by weight, notably at a concentration greater than or equal to 0.1% by weight, in particular greater than or equal to 0.2% by weight in relation to the total weight of the composition.

According to a particular embodiment, the composition includes allantoin and vitamin A. In this case, the weight ratio of allantoin to vitamin A can range from 10 to 1, notably from 2 to 1, and in particular can be about 1.

According to another particular embodiment, the composition includes a sucralfate, polysulfated disaccharide, and/or basic aluminum sucrose sulfate.

The composition can include at least one plant extract, which can be selected in particular from extracts of alchemilla, ivy, horsetail, liquorice, cucumber, arnica, *ginkgo*

*biloba*, echinacea, grape seed, avocado, chamomile, *Centella asiatica, Calendula officinalis, Arnica montana*, hop, rosemary, mallow, periwinkle, orange blossom, green tea, aloe vera and mixtures thereof, and in particular from extracts of *Centella asiatica, Calendula officinalis, Arnica montana* and mixtures thereof.

The plant extracts can be selected for their anti-inflammatory, cicatrizing, sedative, astringent, soothing, smoothing, anti-edema, antioxidant, regenerative, hydrating, antalgic, antiseptic, emollient, protective, hemostatic, anesthetic, bactericidal and/or immunomodulatory properties.

The plant extracts can be used alone or in combination.

The composition can include a total concentration of vegetable extract greater than or equal to 1% by weight, notably a concentration greater than or equal to 2% by weight, in particular greater than or equal to 3% by weight in relation to the total weight of the composition.

The composition can include a total concentration of vegetable extract less than or equal to 15% by weight, notably less than or equal to 10% by weight in relation to the total weight of the composition.

The composition includes a solvent, which includes, or consists of, water.

The used water is purified or sterilized, in particular by sterilizing filtration, in particular via 0.22 µm filtration.

According to a particular embodiment, the composition, notably sterile and/or decontaminated, for topical use includes, or consists of:
  hyaluronic acid at a concentration from 0.1 to 2% by weight, notably from 0.2 to 2% by weight or from 0.1 to 0.5% by weight, in relation to the total weight of the composition,
  at least one skin cicatrization agent selected from:
    allantoin, in a concentration greater than or equal to 0.1% by weight in relation to the total weight of the composition,
    vitamin A, in a concentration greater than or equal to 0.01% by weight in relation to the total weight of the composition,
    sucralfate, and/or
    basic aluminum sucrose sulfate,
  optionally at least one plant extract, and
  at least one solvent.

In addition to the solvent, hyaluronic acid, cicatrization agent and plant extracts, the composition can include a limited number of additional constituents. In particular, it includes only 10, notably only 8, in particular only 6, or only 4, even more particularly only 2 additional constituents.

According to a particular variant it does not include an additional constituent.

The additional constituents are selected to discourage the growth of microorganisms.

The solution can be in the form of a solution, an emulsion, a gel or a micellar solution.

The term "emulsion" refers to a stable and homogeneous mixture of two immiscible liquid substances, in particular in the form of an oil-in-water (O/W) or water-in-oil (W/O) emulsion.

The term "gel" refers to a solution containing in suspension particles sufficiently small so that the mixture is homogeneous, also called a colloidal suspension.

The sensitivity of the formula or composition to bacteria is evaluated according to the method of the European Pharmacopoeia, 6$^{th}$ edition, 2008 (addendum 6.3) and by carrying out a test of effectiveness in order to verify the possible growth of *Aspergillus niger*, the Gram-positive bacteria *Staphylococcus aureus*, the yeast *Candida albicans* and the Gram-negative bacteria *Pseudomonas aeruginosa*.

According to another of its aspects, the invention relates to a unit including a composition of the invention that is packaged in a sealed packaging.

This can notably enable satisfactory preservation of the composition, in particular preservation for a long period and/or preservation at room temperature.

Said packaging can also insulate the composition from the external environment, and in particular shield the composition from light.

The solution can be packaged by filling in a controlled atmosphere or reduced contamination area, or by aseptic filling in a sterile environment, in single dose containers, notably bottles, in multidose containers what allow to protect the solution from contamination during use, notably such as described in the following documents: WO2008/015505, US 2009/0294347, US 2007/0210121, EP 2085068, FR 2816600, U.S. Pat. No. 5,232,687 or FR 2873358, or in any other container, such as bottles, intended for the topical administration of drugs, in particular making it possible to avoid the use of preservatives.

In particular, these packagings can be equipped with delivery systems making it possible to avoid contamination of the composition, notably by filtering the ambient air likely to enter the packaging during use, or by functioning without allowing ambient air to enter.

Particularly, the composition can be located in a flexible pouch on which pressure is applied, for example via pressurized gas, in order to deliver the composition. This type of system can have the advantage of avoiding any entry into the container holding the composition and thus of limiting, even eliminating, the risks of contamination.

The packaging can be selected according to its low permeability to oxygen, nitrogen and nitrogen-based compounds such as nitrates, nitrites, ammonia and phosphates, i.e., products likely either to oxidize the composition or to be a nutrient for the residual bacteria of the composition after treatment.

In particular, the walls constituting the packaging can include materials known for their very low permeability to gases, in particular to oxygen and to water vapor, such as aluminum or ethylene-vinyl alcohol (EVOH) polymers, polyvinylidene chloride (PVDC), polyacrylonitrile (PAN) or polyamide (PA).

These materials can be used alone or in combination with other materials as proposed, for example, in the patent DE 3419255.

The choice of packaging can also be determined by its ability to remain sealed during sterilizing treatment at temperature.

The compositions of the invention are intended for topical use, generally anywhere on the body, and in particular on the eyelids and the related structures of the eye, the hands, the lips and the face.

They can be intended for:
  cleaning the palpebral edge, or free edge of the eyelid, or the face,
  protecting the skin,
  maintaining skin hydration,
  promoting cicatrization, in particular post-operative cicatrization, and/or
  helping to reduce inflammation.

Generally, the compositions of the invention can be used on injured skin, in particular of the face, hands, feet, lips or body having undergone destruction of various origin, such as traumatic, infectious, tumoral, vascular or iatrogenic destruction, and requiring repair corresponding to cicatrization. Particularly, the compositions of the invention make it possible to accelerate cicatrization.

According to a particular embodiment, the compositions of the invention can be used to protect and/or clean the eyelids and the face, notably:

1) in order to eliminate the scales and the crusts from the pathological eyelids of patients suffering from blepharitis,
2) as a cicatrizant after surgeries, such as blepharoplasties, ectropion or lesions, notably cancerous, and/or
3) to prevent and/or treat eye dryness, in particular as a result of the bad general state of the eyelids following the use of drug or chemical treatments or following surgery.

Thus, the invention relates to the topical use of a composition of the invention, or a composition of the invention intended to be used, as a cleaning agent for the palpebral edge or the face, as a skin protector, as a cicatrizant, in particular as a post-operative cicatrizant, and/or as an anti-inflammatory.

The invention further relates to the topical use of a composition of the invention, or a composition, notably pharmaceutical, of the invention intended to be used as:

an agent enabling the elimination of scales and crusts from the pathological eyelids of patients suffering from blepharitis,
as a cicatrizant after surgeries, such as blepharoplasties, and ectropion, or lesions, notably cancerous, and/or
an agent to prevent and/or treat eye dryness, in particular resulting from the bad general state of the eyelids following the use of drug or chemical treatments or following surgery.

The invention also relates to the topical use of a composition of the invention, or a composition, notably pharmaceutical, of the invention intended to be used as an agent:

intended to protect chapped hands, in particular by promoting cicatrization,
intended to protect very dry and chapped lips, in particular by promoting hydration and/or cicatrization,
intended to hydrate and protect skin that is injured or irritated, notably by a pathology, a drug treatment, for example by isotretinoin, or mechanically, for example by dermabrasion, and/or chemically, such by peeling, and/or
intended to protect, hydrate and/or soothe the eyelids following episodes of inflammation, such as eczema.

The invention further relates to a pharmaceutical composition or a drug including, or consisting of, a composition of the invention, in particular such as defined above, and particularly intended to prevent and/or treat one or more indications defined above. The composition of the invention, said drug or said pharmaceutical composition can be intended to prevent and/or treat the indications set out above, in particular eye dryness and pathological eyelids, or further to be intended to enable and/or accelerate cicatrization, in particular following surgeries, such as blepharoplasties, ectropion or lesions, notably cancerous.

According to another of its aspects, the invention relates to a method for preparing a composition including hyaluronic acid, in particular at a concentration greater than or equal to 0.1% by weight in relation to the total weight of the composition, decontaminated and/or sterile, in sealed packaging, including, even consisting of, the following steps consisting in:

a) sterilizing the packaging items, in particular by ionizing treatment or ethylene oxide,
b) purifying the solvent(s), in particular when it includes, or consists of, water, for example by filtration, in particular by filtration on a 0.22 µm filter,
c) when at least one plant extract is present, decontaminating said plant extract, notably by an ionizing treatment, in particular by a ionizing treatment with a value of at least 5 kGy,
d) mixing the components of the composition, notably hyaluronic acid, optionally at least one plant extract and/or one compound having cicatrizing action, in at least one solvent,
e) packaging in a sterile or contamination-controlled environment the composition in a sealed packaging,
f) heating the composition in its sealed packaging, notably using dry heat, in an oven at a temperature ranging from 60 to 95° C., for at least one period of at least 1 hour, followed by cooling at least to room temperature,
g) repeating step f) at least once, notably at least the following day, or the following 2 days, or the following 3 days, and
h) recovering the sealed packaging including the decontaminated and/or sterile composition.

Said process can make it possible to obtain a composition in a sealed container including hyaluronic acid, notably such as described above, in particular in the quantities and ratios described above.

According to a particular embodiment, the method makes it possible to obtain a composition of the invention.

The method notably makes it possible to obtain a composition with a long shelf life without it being necessary to use preservatives and/or EDTA, notably such as described above, while not being destructive to hyaluronic acid.

In particular, this method has no or little effect on the properties of said hyaluronic acid, in particular in relation to its molecular weight.

Hydrophilic compounds such as hyaluronic acid, allantoin and plant extracts can be incorporated in the solvent until total hydration is achieved.

Hydrophobic compounds can be incorporated in the solution in the form of oil-in-water emulsions, liposomes, micelles, dendrimers or another suspension.

The size of the globules incorporated in the solution is variable, however, in the case where the solution including the oil-in-water emulsions is to be filtered the maximum globule size can be less than or equal to 220 nm, in particular less than or equal to 160 nm.

In the case of sterilizing filtration, the globules of the emulsion must be able to pass through a 0.22 µm filter. Globules larger than 220 nm can pass through a 0.22 µm filter by temporarily modifying their shape, however slowing the filtration process.

The heating temperature of step f) can range from 62 to 90° C., and in particular from 65 to 85° C., or from 68 to 80° C.

The heating period of step f) can range from 1 to 3 hours, notably from 1 to 2 hours, in particular from 1 to 1.5 hours, or can be 1 hour.

The heating periods are separated by so-called "RT" periods in which the composition is at room temperature or below, for example 0° C. or less. Said RT periods can range from 5 to 40 hours, notably from 10 to 30 hours, or from 20 to 25 hours.

Particularly, the heating of step f) is carried out over separate periods of at least 5 hours, notably at least 10 hours, even 24 hours.

Step g) can include, or consist of, 1 to 5 repetitions of the heating of step f), in particular 2 to 4 repetitions, even 2 repetitions.

According to another aspect, the invention further relates to a composition likely to be obtained by the method such as defined in the present description.

In particular, the decontamination of step c) is carried out by a treatment using gamma or beta rays of a dose less than or equal to 50 kGy, or a dose less than or equal to 25 kGy, or a dose less than or equal to 5 kGy, so as to decrease the initial microbial load of the plant extracts without altering their properties.

Advantageously, the method makes it possible to obtain a sterile composition while minimally affecting the starting hyaluronic acid, in particular in relation to its molecular weight and/or its chemical organization.

In particular, the method decreases the molecular weight of the hyaluronic acid by less than 20%, notably by less than 10%, in particular by less than 5%.

The choice of the molecular weight of the starting hyaluronic acid, or the combination of hyaluronic acids of various molecular weights, will be carried out so as to obtain after treatment by heating of step f)-g) the desired molecular weight, or the desired combination of molecular weights.

According to still another of its aspects, the invention relates to a composition likely to be obtained, indeed directly obtained, by a method such as defined above.

Of course, the various characteristics presented in the present description can be combined.

The following examples are given to illustrate the invention.

EXAMPLES

Example 1

A composition 1 and a composition 2 including 200 mg of hyaluronic acid of about 800 kDa and about 500 kDa, respectively, in 100 ml of water undergo the heat treatments described in Table 1.

The hyaluronic acids used for these compositions can be for example provided by FIDIA Farmaceutici S.p.A. with the product references HYALOFTIL, HA 1,000,000 Da or HA 500,000 Da, or HTL Biotechnology, manufactured according to the desired molecular weight.

TABLE 1

| Sample | Treatment | Molecular weight (Da) |
| --- | --- | --- |
| Composition 1 | None | 871,400 |
| Composition 1 | 75° C., 15 min | 844,900 |
| Composition 1 | 75° C., 19 min | 856,800 |
| Composition 1 | 80° C., 10 min | 851,200 |
| Composition 2 | None | 565,000 |
| Composition 2 | 75° C., 15 min | 553,000 |
| Composition 2 | 80° C., 10 min | 574,000 |

It emerges from these tests that the molecular weight of the hyaluronic acid present in these compositions is decreased by less than 20%.

Example 2

Three compositions were prepared:
composition A containing a 0.2% concentration of hyaluronic acid of 2 different molecular weights, one between 700 and 750 kDa, the other between 750 and 800 kDa, in a 1:1 proportion in 100 ml of water,
composition B containing a 0.5% concentration of hyaluronic acid of molecular weight between 700 and 750 kDa in 100 ml of water, and
composition C containing a 0.5% concentration of hyaluronic acid of another molecular weight from 750 to 800 kDa in 100 ml of water.

The 3 compositions underwent 3 different temperature treatments:
a treatment at 70° C. for 1 hour followed by cooling once per day for 3 days,
a treatment at 100° C. for 1 hour followed by cooling, and
a treatment at 121° C. for 20 minutes followed by cooling.

TABLE 2

| Sample | Treatment | Molecular weight (Da) |
| --- | --- | --- |
| Composition A | None | 758,000 |
| Composition A | 70° C., 1 h, 3x/24 h | 741,000 |
| Composition A | 100° C., 1 h, 1x | 615,000 |
| Composition A | 121° C., 20 min, 1x | 204,000 |
| Composition B | None | 731,000 |
| Composition B | 70° C., 1 h, 3x/24 h | 696,000 |
| Composition B | 100° C., 1 h, 1x | 398,000 |
| Composition B | 121° C., 20 min, 1x | 291,000 |
| Composition C | None | 750,000 |
| Composition C | 70° C., 1 h, 3x/24 h | 761,000 |
| Composition C | 100° C., 1 h, 1x | 692,000 |
| Composition C | 121° C., 20 min, 1x | 400,000 |

The treatments at 100° C. for 1 hour and 121° C. for 20 minutes lead to significant degradation of the molecular weight of the hyaluronic acid, whereas the treatment at 70° C. for 1 hour followed by cooling to room temperature carried out 3 times at 24-hour intervals did not lead to significant modification of the molecular weight of the hyaluronic acid. Furthermore, in all the samples having undergone heat treatment, the level of microbiological cleanliness was evaluated to be in conformity (<1 CFU/g) and moreover sterile in the context of the European Pharmacopoeia.

The invention claimed is:

1. A preservatives free composition, said composition is decontaminated and/or sterile, for topical use, wherein said composition comprises:
   a combination of
   low molecular weight hyaluronic acid, having a molecular weight below 800 kDa, and —high molecular weight hyaluronic acid having a molecular weight equal to or higher than 800 kDa, at a concentration greater than or equal to 0.1% by weight in relation to the total weight of the composition, wherein said high molecular weight hyaluronic acid has a molecular weight greater than the molecular weight of said low molecular weight hyaluronic acid, and the weight ratio of said high molecular weight hyaluronic acid to said low molecular weight hyaluronic acid ranges from 0.2 to 2,
   at least one skin cicatrization agent, and
   at least one solvent.

2. The composition of claim 1, wherein high molecular weight hyaluronic acid has a molecular weight of 800 to 1200 kDa and wherein low molecular weight hyaluronic acid has a molecular weight of 10 to 600 kDa.

3. The composition of claim 1 wherein said skin cicatrization agent is selected from the group consisting of allantoin, vitamin A and sucralfate.

4. A method for cleaning the palpebral edge in a patient in need thereof comprising applying the composition of claim 1 on the eyelid.

5. A method for preventing and/or treating eye dryness in a patient in need thereof comprising applying the composition of claim 1 on the eyelid.

* * * * *